US011865283B2

(12) United States Patent
Schultz et al.

(10) Patent No.: US 11,865,283 B2
(45) Date of Patent: Jan. 9, 2024

(54) ADJUSTABLE SHUNTING SYSTEMS WITH PLATE ASSEMBLIES, AND ASSOCIATED SYSTEMS AND METHODS

(71) Applicant: Shifamed Holdings, LLC, Campbell, CA (US)

(72) Inventors: Eric Schultz, Los Altos, CA (US); Tom Saul, Moss Beach, CA (US); Michael Drews, Palo Alto, CA (US); Richard Lilly, San Jose, CA (US); Katherine Sapozhnikov, Campbell, CA (US); Robert Chang, Belmont, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 17/774,310

(22) PCT Filed: Jan. 21, 2022

(86) PCT No.: PCT/US2022/013336
§ 371 (c)(1),
(2) Date: May 4, 2022

(87) PCT Pub. No.: WO2022/159723
PCT Pub. Date: Jul. 28, 2022

(65) Prior Publication Data
US 2023/0201544 A1 Jun. 29, 2023

Related U.S. Application Data

(60) Provisional application No. 63/140,655, filed on Jan. 22, 2021.

(51) Int. Cl.
*A61M 27/00* (2006.01)

(52) U.S. Cl.
CPC ..... *A61M 27/002* (2013.01); *A61M 2205/0266* (2013.01); *A61M 2205/3334* (2013.01)

(58) Field of Classification Search
CPC .. A61M 2205/0266; A61M 2205/3334; A61M 27/002; A61M 5/14276;
(Continued)

(56) References Cited

U.S. PATENT DOCUMENTS

| 4,401,107 A | 8/1983 | Harber et al. |
| 4,595,390 A | 6/1986 | Hakim et al. |

(Continued)

FOREIGN PATENT DOCUMENTS

| AU | 2014200171 | 1/2014 |
| AU | 2014201621 B2 | 3/2016 |

(Continued)

OTHER PUBLICATIONS

International Search Report and Written Opinion received for PCT Application No. PCT/US22/35324, filed on Jun. 28, 2022, Applicant: Shifamed Holdings, LLC, dated Nov. 22, 2022, 12 pages.

(Continued)

*Primary Examiner* — Kai H Weng
(74) *Attorney, Agent, or Firm* — Perkins Coie LLP

(57) ABSTRACT

The present technology is generally directed to adjustable shunting systems for draining fluid from a first body region to a second body region. The adjustable shunting systems include a flow control plate or cartridge for controlling the flow of fluid through the system. For example, the flow control plate can include a shape memory actuation assembly having one or more nitinol actuators for controlling the flow of fluid through the system. The flow control plate can further include a plurality of discrete sheets or layers adhered together to encase the shape memory actuation (Continued)

assembly. The discrete sheets or layers can form flow channels for directing fluid through the flow control plate.

11 Claims, 9 Drawing Sheets

(58) Field of Classification Search
CPC ....... A61M 5/16877; A61M 2205/3331; A61F 9/00781; A61F 9/0017; A61F 2009/00891
See application file for complete search history.

(56) References Cited

U.S. PATENT DOCUMENTS

| | | |
|---|---|---|
| 5,070,697 A | 12/1991 | Van Zeggeren |
| 5,123,906 A | 6/1992 | Kelman |
| 5,476,445 A | 12/1995 | Baerveldt et al. |
| 5,601,094 A | 2/1997 | Reiss |
| 6,077,298 A | 6/2000 | Tu et al. |
| 6,077,299 A | 6/2000 | Adelberg et al. |
| 6,203,513 B1 | 3/2001 | Yaron et al. |
| 6,261,256 B1 | 7/2001 | Ahmed |
| 6,450,984 B1 | 9/2002 | Lynch et al. |
| 6,508,779 B1 | 1/2003 | Suson |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,736,791 B1 | 5/2004 | Tu et al. |
| 6,789,447 B1 | 9/2004 | Zinck |
| 7,025,740 B2 | 4/2006 | Ahmed |
| 7,207,965 B2 | 4/2007 | Simon |
| 7,354,416 B2 | 4/2008 | Quiroz-Mereado et al. |
| 7,458,953 B2 | 12/2008 | Peyman |
| 7,699,882 B2 | 4/2010 | Stamper et al. |
| 7,717,872 B2 | 5/2010 | Shetty |
| 7,947,008 B2 | 5/2011 | Grahn et al. |
| 8,012,134 B2 | 9/2011 | Claude et al. |
| 8,206,333 B2 | 6/2012 | Schmidt et al. |
| 8,206,440 B2 | 6/2012 | Guarnieri |
| 8,298,240 B2 | 10/2012 | Giger et al. |
| 8,308,701 B2 | 11/2012 | Horvath et al. |
| 8,414,635 B2 | 4/2013 | Hyodoh et al. |
| 8,506,515 B2 | 8/2013 | Burns et al. |
| 8,540,659 B2 | 9/2013 | Berlin |
| 8,579,848 B2 | 11/2013 | Field et al. |
| 8,585,629 B2 | 11/2013 | Grabner et al. |
| 8,663,303 B2 | 3/2014 | Horvath et al. |
| 8,702,639 B2 | 4/2014 | Van Der Mooren et al. |
| 8,721,702 B2 | 5/2014 | Romoda et al. |
| 8,753,305 B2 | 6/2014 | Field et al. |
| 8,758,290 B2 | 6/2014 | Horvath et al. |
| 8,765,210 B2 | 7/2014 | Romoda et al. |
| 8,771,220 B2 | 7/2014 | Nissan et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,882,781 B2 | 11/2014 | Smedley et al. |
| 8,915,877 B2 | 12/2014 | Cunningham et al. |
| 8,974,511 B2 | 3/2015 | Horvath et al. |
| 9,017,276 B2 | 4/2015 | Horvath et al. |
| 9,095,411 B2 | 8/2015 | Horvath et al. |
| 9,095,413 B2 | 8/2015 | Romoda et al. |
| 9,113,994 B2 | 8/2015 | Horvath et al. |
| 9,125,723 B2 | 9/2015 | Horvath et al. |
| 9,192,516 B2 | 11/2015 | Horvath et al. |
| 9,226,851 B2 | 1/2016 | Gunn |
| 9,271,869 B2 | 3/2016 | Horvath et al. |
| 9,283,115 B2 | 3/2016 | Lind et al. |
| 9,283,116 B2 | 3/2016 | Romoda et al. |
| 9,289,324 B2 | 3/2016 | Johnson et al. |
| 9,326,891 B2 | 5/2016 | Horvath et al. |
| 9,375,347 B2 | 6/2016 | Stergiopulos |
| 9,393,153 B2 | 7/2016 | Horvath et al. |
| 9,555,410 B2 | 1/2017 | Brammer et al. |
| 9,585,789 B2 | 3/2017 | Silvestrini et al. |
| 9,585,790 B2 | 3/2017 | Horvath et al. |
| 9,592,154 B2 | 3/2017 | Romoda et al. |
| 9,610,195 B2 | 4/2017 | Horvath |
| 9,636,254 B2 | 5/2017 | Yu et al. |
| 9,636,255 B2 | 5/2017 | Haffner et al. |
| 9,655,778 B2 | 5/2017 | Tyler |
| 9,655,779 B2 | 5/2017 | Bigler et al. |
| 9,693,900 B2 | 7/2017 | Gallardo Inzunza |
| 9,693,901 B2 | 7/2017 | Horvath et al. |
| 9,757,276 B2 | 9/2017 | Penhasi |
| 9,808,373 B2 | 11/2017 | Horvath et al. |
| 9,877,866 B2 | 1/2018 | Horvath et al. |
| 9,883,969 B2 | 2/2018 | Horvath et al. |
| 9,980,854 B2 | 5/2018 | Horvath et al. |
| 10,004,638 B2 | 6/2018 | Romoda et al. |
| 10,080,682 B2 | 9/2018 | Horvath et al. |
| 10,085,884 B2 | 10/2018 | Reitsamer et al. |
| 10,154,924 B2 | 12/2018 | Clauson et al. |
| 10,159,600 B2 | 12/2018 | Horvath et al. |
| 10,195,078 B2 | 2/2019 | Horvath et al. |
| 10,195,079 B2 | 2/2019 | Horvath et al. |
| 10,231,871 B2 | 3/2019 | Hill |
| 10,238,536 B2 | 3/2019 | Olson et al. |
| 10,285,853 B2 | 5/2019 | Rangel-Friedman et al. |
| 10,307,293 B2 | 6/2019 | Horvath et al. |
| 10,314,743 B2 | 6/2019 | Romoda et al. |
| 10,322,267 B2 | 6/2019 | Hakim |
| 10,369,048 B2 | 8/2019 | Horvath et al. |
| 10,405,903 B1 | 9/2019 | Biesinger et al. |
| 10,335,030 B2 | 10/2019 | Alhourani |
| 10,342,703 B2 | 11/2019 | Siewert et al. |
| 10,463,537 B2 | 11/2019 | Horvath et al. |
| 10,470,927 B2 | 11/2019 | Horvath et al. |
| 10,363,168 B2 | 12/2019 | Schieber et al. |
| 10,492,948 B2 | 12/2019 | Baerveldt |
| 10,524,959 B2 | 1/2020 | Horvath |
| 10,524,958 B2 | 3/2020 | Camras et al. |
| 10,596,035 B2 | 4/2020 | Stergiopulos et al. |
| 10,758,412 B2 | 4/2020 | Velasquez |
| 10,716,663 B2 | 7/2020 | Salahich et al. |
| 11,122,975 B2 | 1/2021 | Rodger et al. |
| 10,912,675 B2 | 2/2021 | Lubatschowski |
| 11,166,847 B2 | 2/2021 | Badawi et al. |
| 10,952,897 B1 | 3/2021 | Smith |
| 10,960,074 B2 | 3/2021 | Berdahl |
| 11,007,061 B2 | 5/2021 | Passman et al. |
| 11,039,954 B2 | 6/2021 | Cohen et al. |
| 11,058,581 B2 | 7/2021 | Mixter et al. |
| 11,065,154 B1 | 7/2021 | Sponsel et al. |
| 11,083,624 B2 | 8/2021 | Stein et al. |
| 11,166,848 B2 | 11/2021 | Mixter et al. |
| 11,166,849 B2 | 11/2021 | Mixter et al. |
| 11,291,585 B2 | 4/2022 | Schultz et al. |
| 11,517,477 B2 | 12/2022 | Lilly et al. |
| 11,529,258 B2 | 12/2022 | Chang et al. |
| 11,596,550 B2 | 3/2023 | Chang et al. |
| 2001/0011585 A1 | 8/2001 | Cassidy et al. |
| 2002/0177891 A1 | 11/2002 | Miles et al. |
| 2002/0193725 A1 | 12/2002 | Odrich |
| 2003/0127090 A1 | 7/2003 | Gifford et al. |
| 2003/0163079 A1 | 8/2003 | Burnett |
| 2003/0183008 A1 | 10/2003 | Bang et al. |
| 2004/0010219 A1 | 1/2004 | McCusker et al. |
| 2004/0190153 A1 | 9/2004 | Esch |
| 2004/0193095 A1 | 9/2004 | Shadduck |
| 2004/0254520 A1 | 12/2004 | Porteous et al. |
| 2005/0049578 A1 | 3/2005 | Tu et al. |
| 2005/0059956 A1 | 3/2005 | Varner et al. |
| 2005/0196424 A1 | 9/2005 | Chappa |
| 2006/0004317 A1 | 1/2006 | Mauge et al. |
| 2006/0069340 A1 | 3/2006 | Simon |
| 2006/0155300 A1 | 7/2006 | Stamper et al. |
| 2006/0276739 A1 | 12/2006 | Brown |
| 2007/0010837 A1 | 1/2007 | Tanaka |
| 2007/0078371 A1 | 4/2007 | Brown et al. |
| 2007/0088432 A1 | 4/2007 | Solovay et al. |
| 2007/0265646 A1 | 11/2007 | McCoy et al. |
| 2007/0299487 A1 | 12/2007 | Shadduck |

(56) References Cited

U.S. PATENT DOCUMENTS

| | | |
|---|---|---|
| 2008/0077071 A1 | 3/2008 | Yaron et al. |
| 2008/0119891 A1 | 5/2008 | Miles et al. |
| 2008/0125691 A1 | 5/2008 | Yaron et al. |
| 2008/0277332 A1 | 11/2008 | Liu |
| 2009/0012483 A1 | 1/2009 | Blott et al. |
| 2009/0036818 A1 | 2/2009 | Grahn et al. |
| 2009/0043321 A1 | 2/2009 | Conston et al. |
| 2009/0243956 A1 | 10/2009 | Keilman et al. |
| 2009/0287136 A1 | 11/2009 | Castillejos |
| 2009/0314970 A1 | 12/2009 | MCAvoy et al. |
| 2009/0326517 A1 | 12/2009 | Bork et al. |
| 2010/0114006 A1 | 5/2010 | Baerveldt |
| 2010/0234791 A1 | 9/2010 | Lynch et al. |
| 2010/0241077 A1 | 9/2010 | Geipel et al. |
| 2010/0249691 A1 | 9/2010 | Van Der Mooren et al. |
| 2011/0105986 A1 | 5/2011 | Bronstein et al. |
| 2012/0035525 A1 | 2/2012 | Silvestrini |
| 2012/0065570 A1 | 3/2012 | Yeung et al. |
| 2012/0089073 A1 | 4/2012 | Cunningham, Jr. |
| 2012/0232461 A1 | 9/2012 | Seaver et al. |
| 2013/0085440 A1 | 4/2013 | Bohm et al. |
| 2013/0131577 A1 | 5/2013 | Bronstein et al. |
| 2013/0150773 A1 | 6/2013 | Nissan et al. |
| 2013/0150776 A1 | 6/2013 | Bohm et al. |
| 2013/0158381 A1 | 6/2013 | Rickard |
| 2013/0197621 A1 | 8/2013 | Ryan et al. |
| 2013/0199646 A1 | 8/2013 | Brammer et al. |
| 2013/0205923 A1 | 8/2013 | Brammer et al. |
| 2013/0211312 A1 | 8/2013 | Gelvin |
| 2013/0267887 A1 | 10/2013 | Kahook et al. |
| 2013/0317412 A1 | 11/2013 | Dacquay et al. |
| 2013/0338564 A1 | 12/2013 | Rickard et al. |
| 2014/0046439 A1 | 2/2014 | Dos Santos et al. |
| 2014/0081195 A1 | 3/2014 | Clauson et al. |
| 2014/0309611 A1 | 10/2014 | Wilt et al. |
| 2015/0011926 A1 | 1/2015 | Reitsamer et al. |
| 2015/0034217 A1 | 2/2015 | Vad |
| 2015/0045716 A1 | 2/2015 | Gallardo Inzunza |
| 2015/0142049 A1 | 5/2015 | Delgado et al. |
| 2015/0230843 A1 | 8/2015 | Palmer et al. |
| 2015/0265469 A1 | 9/2015 | Olson et al. |
| 2015/0313603 A1 | 11/2015 | Bodewadt et al. |
| 2016/0151179 A1 | 6/2016 | Favier et al. |
| 2016/0220794 A1 | 8/2016 | Negre |
| 2016/0256317 A1 | 9/2016 | Horvath et al. |
| 2016/0256318 A1 | 9/2016 | Horvath et al. |
| 2016/0256319 A1 | 9/2016 | Horvath et al. |
| 2016/0256320 A1 | 9/2016 | Horvath et al. |
| 2016/0287439 A1 | 10/2016 | Stergiopulos |
| 2016/0354244 A1 | 12/2016 | Horvath et al. |
| 2016/0354245 A1 | 12/2016 | Horvath et al. |
| 2017/0027582 A1 | 2/2017 | Khoury et al. |
| 2017/0071791 A1 | 3/2017 | Piven |
| 2017/0087016 A1 | 3/2017 | Camras |
| 2017/0172797 A1 | 6/2017 | Horvath et al. |
| 2017/0172798 A1 | 6/2017 | Horvath et al. |
| 2017/0172799 A1 | 6/2017 | Horvath |
| 2017/0312125 A1 | 11/2017 | Clauson et al. |
| 2017/0348149 A1 | 12/2017 | Stergiopulos et al. |
| 2017/0348150 A1 | 12/2017 | Horvath et al. |
| 2018/0014828 A1 | 1/2018 | Fonte et al. |
| 2018/0028361 A1 | 2/2018 | Haffner et al. |
| 2018/0028366 A1 | 2/2018 | Tout et al. |
| 2018/0092775 A1 | 4/2018 | de Juan, Jr. et al. |
| 2018/0147089 A1 | 5/2018 | Horvath et al. |
| 2018/0177633 A1 | 6/2018 | Haffner et al. |
| 2018/0206878 A1 | 7/2018 | Uspenski et al. |
| 2018/0250166 A1 | 9/2018 | Lubatschowski |
| 2018/0333296 A1 | 11/2018 | Heitzmann et al. |
| 2019/0000673 A1 | 1/2019 | Fjield et al. |
| 2019/0021907 A1 | 1/2019 | Horvath et al. |
| 2019/0038462 A1 | 2/2019 | Vandiest et al. |
| 2019/0046356 A1 | 2/2019 | Laroche |
| 2019/0060118 A1 | 2/2019 | Hill |
| 2019/0133826 A1 | 3/2019 | Horvath et al. |
| 2019/0121278 A1 | 4/2019 | Kawamura et al. |
| 2019/0142632 A1 | 5/2019 | Badawi et al. |
| 2019/0151079 A1 | 5/2019 | Zaldivar |
| 2019/0167475 A1 | 6/2019 | Horvath et al. |
| 2019/0240069 A1 | 8/2019 | Horvath et al. |
| 2019/0247231 A1 | 8/2019 | McClunan |
| 2019/0254873 A1 | 8/2019 | Carras et al. |
| 2019/0274881 A1 | 9/2019 | Romoda et al. |
| 2019/0274882 A1 | 9/2019 | Romoda et al. |
| 2019/0307608 A1 | 10/2019 | Lee et al. |
| 2019/0344057 A1 | 11/2019 | Cima et al. |
| 2019/0350758 A1 | 11/2019 | Horvath et al. |
| 2019/0353269 A1 | 11/2019 | Ossmer et al. |
| 2019/0358086 A1 | 11/2019 | Camras et al. |
| 2019/0374384 A1 | 12/2019 | Xie et al. |
| 2020/0069469 A1 | 3/2020 | Horvath et al. |
| 2020/0085620 A1 | 3/2020 | Euteneuer et al. |
| 2020/0121503 A1 | 4/2020 | Badawi et al. |
| 2020/0121504 A1 | 4/2020 | Stegmann et al. |
| 2020/0129332 A1 | 4/2020 | Van Der Mooren et al. |
| 2020/0170839 A1 | 6/2020 | Borrmann et al. |
| 2020/0179171 A1 | 6/2020 | Crimaldi et al. |
| 2020/0214891 A1 | 7/2020 | Bigler et al. |
| 2020/0229977 A1 | 7/2020 | Mixter et al. |
| 2020/0229980 A1 | 7/2020 | Horvath |
| 2020/0229981 A1 | 7/2020 | Mixter et al. |
| 2020/0229982 A1 | 7/2020 | Mixter et al. |
| 2020/0246188 A1 | 8/2020 | Horvath et al. |
| 2020/0253725 A1 | 8/2020 | Hadba et al. |
| 2020/0261271 A1 | 8/2020 | Horvath et al. |
| 2020/0276050 A1 | 9/2020 | Simons et al. |
| 2020/0306086 A1 | 10/2020 | Da Silva Curiel et al. |
| 2020/0345549 A1 | 11/2020 | Lu et al. |
| 2021/0015665 A1 | 1/2021 | Hacker et al. |
| 2021/0030590 A1 | 2/2021 | Blanda et al. |
| 2021/0038158 A1 | 2/2021 | Haffner et al. |
| 2021/0069486 A1 | 3/2021 | Hakim |
| 2021/0106462 A1 | 4/2021 | Sherwood et al. |
| 2021/0128357 A1 | 5/2021 | de Juan, Jr. et al. |
| 2021/0137736 A1 | 5/2021 | Cavuto et al. |
| 2021/0161713 A1 | 6/2021 | Bouremel et al. |
| 2021/0196516 A1 | 7/2021 | Lanchulev |
| 2021/0205132 A1 | 7/2021 | Horvath et al. |
| 2021/0212858 A1 | 7/2021 | Tran et al. |
| 2021/0251806 A1 | 8/2021 | Schultz et al. |
| 2021/0282922 A1 | 9/2021 | Cohen-Tzemaeh et al. |
| 2021/0298948 A1 | 9/2021 | Haffner et al. |
| 2021/0315806 A1 | 10/2021 | Haffner |
| 2021/0330499 A1 | 10/2021 | Wardle et al. |
| 2022/0087865 A1 | 3/2022 | Argento et al. |
| 2022/0142818 A1 | 5/2022 | Chang et al. |
| 2022/0160545 A1 | 5/2022 | Mixter et al. |
| 2022/0160546 A1 | 5/2022 | Mixter et al. |
| 2022/0168146 A1 | 6/2022 | Badawi et al. |
| 2022/0202613 A1 | 6/2022 | Chang et al. |
| 2022/0241565 A1 | 8/2022 | Nae et al. |
| 2022/0273491 A1 | 9/2022 | Brown |
| 2022/0339035 A1 | 10/2022 | Lilly et al. |
| 2022/0354695 A1 | 11/2022 | Badawi et al. |
| 2022/0387216 A1 | 12/2022 | Schultz et al. |
| 2022/0387217 A1 | 12/2022 | Argento et al. |
| 2023/0086856 A1 | 3/2023 | Chang et al. |
| 2023/0092196 A1 | 3/2023 | Argento et al. |

FOREIGN PATENT DOCUMENTS

| | | |
|---|---|---|
| AU | 2016201445 B2 | 3/2016 |
| AU | 2018200325 A1 | 2/2018 |
| AU | 2017274654 | 12/2018 |
| AU | 2020201818 | 4/2020 |
| AU | 2017439185 | 5/2020 |
| AU | 2018412569 | 10/2020 |
| BR | 112017025859 A2 | 8/2018 |
| BR | 112020008969 | 10/2020 |
| CA | 2987953 A1 | 12/2016 |
| CA | 3080713 | 5/2019 |
| CA | 3093160 | 9/2019 |
| CN | 104490515 | 4/2015 |
| CN | 106726124 | 5/2017 |

(56) References Cited

FOREIGN PATENT DOCUMENTS

| | | |
|---|---|---|
| CN | 108743016 A | 11/2018 |
| CN | 111405875 | 7/2020 |
| CO | 2020011460 | 11/2020 |
| DE | 10217061 | 3/2003 |
| DE | 102010015447 A1 | 10/2011 |
| DE | 102017124885 A1 | 4/2019 |
| DE | 102018112065 A1 | 11/2019 |
| DE | 102019204846 A1 | 10/2020 |
| EP | 1292256 A1 | 3/2003 |
| EP | 1737531 A2 | 1/2007 |
| EP | 2552369 | 1/2017 |
| EP | 3302381 A1 | 4/2018 |
| EP | 1765234 | 10/2019 |
| EP | 2999430 | 11/2019 |
| EP | 2677981 | 4/2020 |
| EP | 3659495 | 6/2020 |
| EP | 3518846 | 8/2020 |
| EP | 3666236 | 8/2020 |
| EP | 3687374 | 8/2020 |
| EP | 3706653 | 9/2020 |
| EP | 3730104 | 10/2020 |
| EP | 3735947 | 11/2020 |
| EP | 3773377 | 2/2021 |
| EP | 3846747 | 7/2021 |
| EP | 3846748 | 7/2021 |
| EP | 3329884 | 8/2021 |
| EP | 2389138 | 9/2021 |
| EP | 3870120 | 9/2021 |
| EP | 3313335 | 11/2021 |
| ES | 2725550 | 9/2019 |
| HK | 1252748 | 5/2019 |
| HU | E043303 | 8/2019 |
| JP | 5576427 B2 | 8/2014 |
| JP | 2018519892 | 7/2018 |
| JP | 2018130580 | 8/2018 |
| JP | 2019517366 | 6/2019 |
| JP | 2019205934 | 12/2019 |
| JP | 2020049361 | 4/2020 |
| KR | 2018015684 A | 2/2018 |
| KR | 20190019966 | 2/2019 |
| KR | 20200021551 | 2/2020 |
| KR | 20200059305 | 5/2020 |
| PL | 2640455 | 8/2019 |
| PT | 2640455 | 5/2019 |
| RU | 2687764 | 5/2019 |
| RU | 2018142990 | 6/2020 |
| SG | 11202008604 | 10/2020 |
| TR | 201906873 | 6/2019 |
| WO | WO2004081613 | 9/2004 |
| WO | WO2007011302 A1 | 1/2007 |
| WO | WO2010111528 | 9/2010 |
| WO | WO2014130574 | 8/2014 |
| WO | WO2016100500 | 6/2016 |
| WO | WO2016149425 | 9/2016 |
| WO | WO2016196841 A1 | 12/2016 |
| WO | WO2018229766 | 12/2018 |
| WO | WO2019094004 A1 | 5/2019 |
| WO | WO2019165053 | 8/2019 |
| WO | WO2019172940 | 9/2019 |
| WO | WO2020150663 | 7/2020 |
| WO | WO2020215068 | 10/2020 |
| WO | WO2020223491 | 11/2020 |
| WO | WO2020231993 | 11/2020 |
| WO | WO2020247365 | 12/2020 |
| WO | WO2020261184 | 12/2020 |
| WO | WO2021007294 | 1/2021 |
| WO | WO2021007296 | 1/2021 |
| WO | WO2021028703 | 2/2021 |
| WO | WO2021068078 | 4/2021 |
| WO | WO2021072315 | 4/2021 |
| WO | WO2021072317 | 4/2021 |
| WO | WO2021113730 | 6/2021 |
| WO | WO2021142255 | 7/2021 |
| WO | WO2021151007 | 7/2021 |
| WO | WO2021163566 | 8/2021 |
| WO | WO2021168130 | 8/2021 |
| WO | WO2021174298 | 9/2021 |
| WO | WO2021176332 | 9/2021 |
| WO | WO2021188952 | 9/2021 |
| WO | WO2021204312 | 10/2021 |
| WO | WO2021212007 | 10/2021 |
| WO | WO2021230887 | 11/2021 |
| WO | WO2022175681 | 8/2022 |
| WO | WO2022220861 | 10/2022 |
| WO | WO2023004067 | 1/2023 |
| WO | WO2023278452 | 1/2023 |
| WO | WO2023009366 | 2/2023 |
| WO | WO2023063961 | 4/2023 |
| WO | WO2023064491 | 4/2023 |
| WO | WO2023091307 | 5/2023 |
| WO | WO2023107486 | 6/2023 |
| ZA | 201708295 | 5/2020 |

OTHER PUBLICATIONS

International Search Report and Written Opinion received for PCT Application No. PCT/US22/37917, filed on Jul. 21, 2022, Applicant: Shifamed Holdings, LLC, dated Dec. 15, 2022, 15 pages.

Keulegan et al. "Pressure Losses for Fluid Flow in Curved Pipes," Journal of Research of the National Bureau of Standards, vol. 18, Jan. 31, 1937 (Jan. 31, 1937), 26 pages.

Olsen et al. "Human sclera: thickness and surface area," American Journal of Ophthalmology, vol. 125, Issue. 2, https://pubmed.ncbi.nlm.nih.gov/9467451, Feb. 1, 1998 (Feb. 1, 1998), 1 page.

International Search Report and Written Opinion received for PCT Application No. PCT/US22/048863, filed on Nov. 3, 2022, Applicant: Shifamed Holdings, LLC, dated Feb. 16, 2023, 13 pages.

International Search Report and Written Opinion received for PCT Application No. PCT/US18/43158, filed on Jul. 20, 2018, Applicant: Shifamed Holdings, LLC, dated Nov. 23, 2018, 12 pages.

International Search Report and Written Opinion received for PCT Application No. PCT/US20/14186, filed on Jan. 17, 2020, Applicant: Shifamed Holdings, LLC, dated Jun. 4, 2020, 13 pages.

International Search Report and Written Opinion received for PCT Application No. PCT/US21/14774, filed on Jan. 22, 2021, Applicant: Shifamed Holdings, LLC, dated May 12, 2021, 10 pages.

International Search Report and Written Opinion received for PCT Application No. PCT/US21/17962, filed on Feb. 12, 2021, Applicant: Shifamed Holdings, LLC, dated Jun. 7, 2021, 12 pages.

International Search Report and Written Opinion received for PCT Application No. PCT/US21/23238, filed on Mar. 19, 2021, Applicant: Shifamed Holdings, LLC, dated Jul. 8, 2021, 10 pages.

International Search Report and Written Opinion received for PCT Application No. PCT/US21/18601, filed on Feb. 18, 2021, Applicant: Shifamed Holdings, LLC, dated Jul. 19, 2021, 12 pages.

International Search Report and Written Opinion received for PCT Application No. PCT/US21/27742, filed on Apr. 16, 2021, Applicant: Shifamed Holdings, LLC, dated Oct. 7, 2021, 13 pages.

International Search Report and Written Opinion received for PCT Application No. PCT/US21/49140, filed on Sep. 3, 2021, Applicant: Shifamed Holdings, LLC, dated Dec. 7, 2021, 22 pages.

International Search Report and Written Opinion received for PCT Application No. PCT/US21/55258, filed on Oct. 15, 2021, Applicant: Shifamed Holdings, LLC, dated Feb. 28, 2022, 18 pages.

International Search Report and Written Opinion received for PCT Application No. PCT/US20/55144, filed on Oct. 9, 2020, Applicant: Shifamed Holdings, LLC, dated Feb. 1, 2021, 16 pages.

International Search Report and Written Opinion received for PCT Application No. PCT/US20/55141, filed on Oct. 9, 2020, Applicant: Shifamed Holdings, LLC, dated Jan. 29, 2021, 11 pages.

International Search Report and Written Opinion received for PCT Application No. PCT/US22/13336, filed on Jan. 21, 2022, Applicant: Shifamed Holdings, LLC, dated Apr. 11, 2022, 9 pages.

International Search Report and Written Opinion received for PCT Application No. PCT/US22/52002, filed on Dec. 6, 2022, Applicant: Shifamed Holdings, LLC, dated Mar. 21, 2023, 11 pages.

(56) References Cited

OTHER PUBLICATIONS

International Search Report and Written Opinion received for PCT Application No. PCT/US22/46604, filed on Oct. 13, 2022, Applicant: Shifamed Holdings, LLC, dated Mar. 30, 2023, 11 pages.

ADJUSTABLE SHUNTING SYSTEMS WITH PLATE ASSEMBLIES, AND ASSOCIATED SYSTEMS AND METHODS

CROSS-REFERENCE TO RELATED APPLICATIONS

This application is a 35 U.S.C. § 371 U.S. National Phase application of International Patent Application No. PCT/US2022/013336, filed Jan. 21, 2022, and titled ADJUSTABLE SHUNTING SYSTEMS WITH PLATE ASSEMBLIES, AND ASSOCIATED SYSTEMS AND METHODS, which claims priority to U.S. Provisional Patent Application No. 63/140,655, filed Jan. 22, 2021, each of which is herein incorporated by reference in its entirety.

TECHNICAL FIELD

The present technology generally relates to implantable medical devices and, in particular, to intraocular shunting systems and associated methods for selectively controlling fluid flow between different portions of a patient's eye.

BACKGROUND

Glaucoma is a degenerative ocular condition involving damage to the optic nerve that can cause progressive and irreversible vision loss. Glaucoma is frequently associated with ocular hypertension, an increase in pressure within the eye resultant from an increase in production of aqueous humor ("aqueous") within the eye and/or a decrease in the rate of outflow of aqueous from within the eye into the blood stream. Aqueous is produced in the ciliary body at the boundary of the posterior and anterior chambers of the eye. It flows into the anterior chamber and eventually into the capillary bed in the sclera of the eye. Glaucoma is typically caused by a failure in mechanisms that transport aqueous out of the eye and into the blood stream.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

Figure 1:
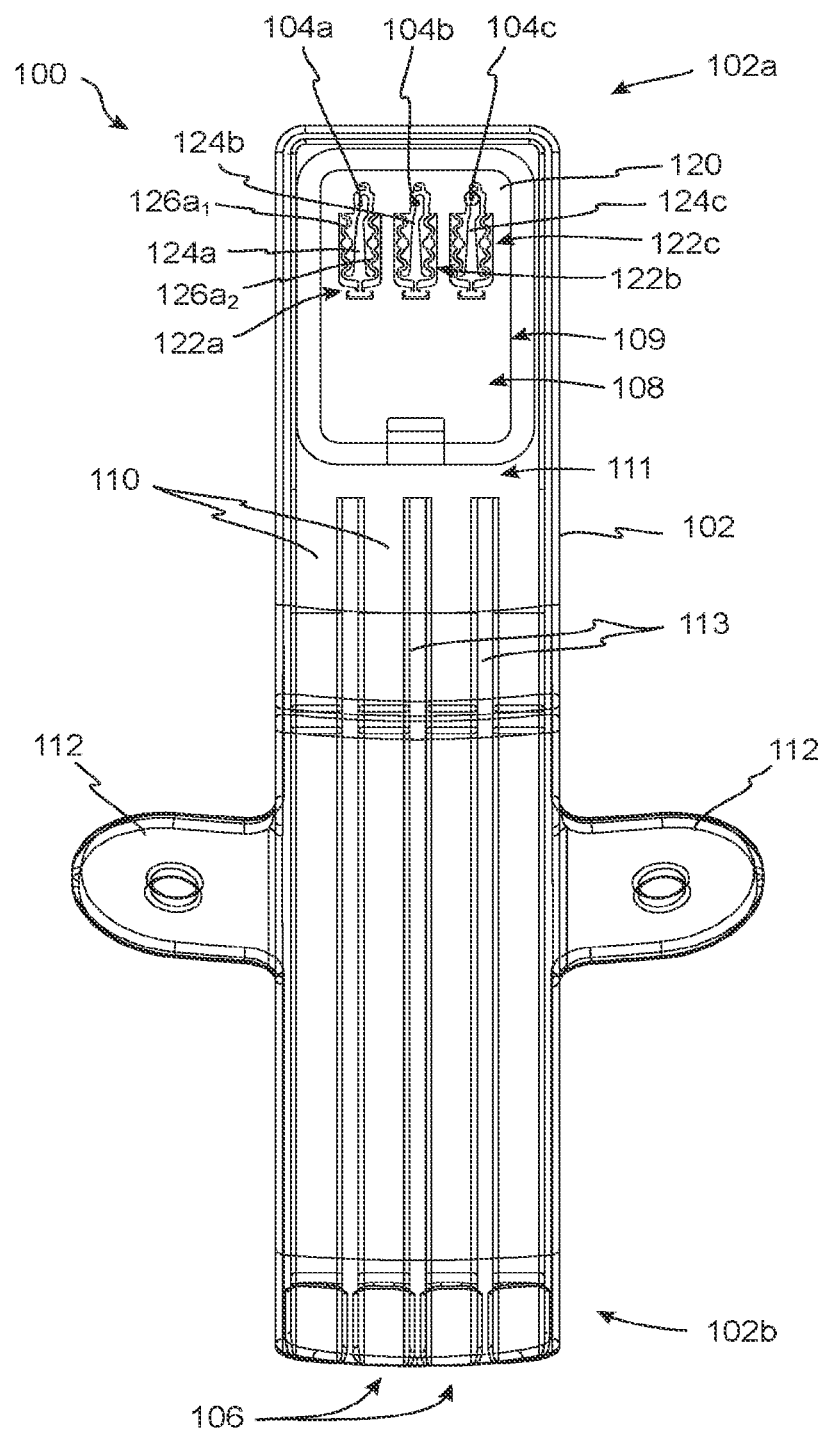
FIG. 1 illustrates an intraocular shunting system configured in accordance with select embodiments of the present technology.

The present technology is generally directed to adjustable shunting systems for draining fluid from a first body region to a second body region. The adjustable shunting systems include a plate assembly (e.g., a flow control plate or cartridge) for controlling the flow of fluid through the system. For example, the plate assembly can include a shape memory actuation assembly having one or more nitinol actuators for controlling the flow of fluid through the system. The plate assembly can further include a plurality of discrete sheets or layers adhered together to encase the shape memory actuation assembly. The discrete sheets or layers can form flow channels for directing fluid through the flow control plate.

The terminology used in the description presented below is intended to be interpreted in its broadest reasonable manner, even though it is being used in conjunction with a detailed description of certain specific embodiments of the present technology. Certain terms may even be emphasized below however, any terminology intended to be interpreted in any restricted manner will be overtly and specifically defined as such in this Detailed Description section. Additionally, the present technology can include other embodiments that are within the scope of the examples hut are not described in detail with respect to FIGS. 1-6.

Reference throw out this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

As used herein, the use of relative terminology, such as "about", "approximately", "substantially" and the like refer to the stated value plus or minus ten percent. For example, the use of the term "about 100" refers to a range of from 90 to 110, inclusive. In instances in which the context requires otherwise and/or relative terminology is used in reference to something that does not include a numerical value, the terms are given their ordinary meaning to one skilled in the art. Reference throughout this specification to the term "resistance" refers to fluid resistance unless the context clearly dictates otherwise. The terms "drainage rate" and "flow" are used interchangeably to describe the movement of fluid through a structure.

Although certain embodiments herein are described in terms of shunting fluid from an anterior chamber of an eye, one of skill in the art will appreciate that the present technology can be readily adapted to shunt fluid from and/or between other portions of the eye, or, more generally, from and/or between a first body region and a second body region. Moreover, while the certain embodiments herein are described in the context of glaucoma treatment, any of the embodiments herein, including those referred to as "glaucoma shunts" or "glaucoma devices" may nevertheless be used and/or modified to treat other diseases or conditions, including other diseases or conditions of the eye or other body regions. For example, the systems described herein can be used to treat diseases characterized by increased pressure and/or fluid build-up, including but not limited to heart failure (e.g., heart failure with preserved ejection fraction, heart failure with reduced ejection fraction, etc.), pulmonary failure, renal failure, hydrocephalus, and the like. Moreover, while generally described in terms of shunting aqueous, the systems described herein may be applied equally to shunting other fluid, such as blood or cerebrospinal fluid, between the first body region and the second body region.

FIG. 1 illustrates an intraocular shunting system ("the system 100") configured in accordance with select embodiments of the present technology. As described in greater detail below, the system 100 is configured to provide an adjustable therapy for draining fluid from a first body region, such as to drain aqueous from an anterior chamber of a patient's eye.

The system 100 includes a generally elongated housing 102 and a plate assembly 120. The elongated housing 102 (which can also be referred to as a casing, membrane, shunting element, or the like) extends between a first end portion 102a and a second end portion 102b. The elongated housing 102 includes a window or other opening 109 providing access to a chamber 108, which, as described in greater detail below, is configured to receive and house the plate assembly 120. The elongated housing 102 further includes a manifold or fluid collection area 111, and one or inure main fluid conduits 110 fluidly coupling the manifold 111 to one or more fluid outlets 106 positioned proximate the second end portion 102b. In some embodiments, the elongated housing 102 is composed of a slightly elastic or flexible biocompatible material (e.g., silicone, etc.). In some embodiments, the elongated housing can have one or more ridges 113 to prevent the main fluid conduit(s) 110 from collapsing. The elongated housing 102 can also have one or more wings or appendages 112 having holes (e.g., suture holes) for securing the elongated housing 102 in a desired position.

The plate assembly 120 (which can also be referred to as a flow control plate, a flow control cartridge, a plate structure, or the like) is positioned within the chamber 108 and is configured to control the flow of fluid through the system 100. For example, the plate assembly 120 includes one or more fluid inlets 104 (e.g., a first fluid inlet 104a, a second fluid inlet 104b, and a third inlet 104c) that permit fluid to enter the plate assembly 120 (and thus the elongated housing 102) from an environment external to the system 100. In some embodiments, the upper surface of the plate assembly 120 forms a substantial fluid seal with the elongated housing 102 such that the only way for fluid to enter the system 100 is through the fluid inlets 104.

The plate assembly 120 is configured to selectively control the flow of fluid entering the system 100. For example, the plate assembly 120 includes a first actuator 122a configured to control the flow of fluid through the first fluid inlet 104a, a second actuator 122b configured to control the flow of fluid through the second fluid inlet 104b, and a third actuator 122c configured to control the flow of fluid through the third fluid inlet 104c. In particular, the first actuator 122a can include a first projection or gating element 124a configured to moveably interface with the first, fluid inlet, 104a, e.g., to move between a first open position in which the first gating element 124a does not substantially prevent fluid from flowing through the first fluid inlet 104a and a second closed position in which the first gating element 124a substantially prevents fluid from flowing through the first fluid inlet 104a. The second actuator 122b can include a second gating element 124b and the third actuator 122c can include a third gating element 124c that operate in a similar manner as the first gating element 124a (e.g., moveable between open and closed positions relative to the second fluid inlet 104b and the third fluid inlet 104c).

The first actuator 122a can further include a first actuation element $126a_1$ and a second actuation element $126a_2$ that drive movement of the first gating element 124a between the open position and the closed position. The first actuation element $126a_1$ and the second actuation element $126a_2$ can be composed at least partially of a shape memory material or alloy (e.g., nitinol). Accordingly, the first actuation element $126a_1$ and the second actuation element $126a_2$ can be transitionable at least between a first material phase or state (e.g., a martensitic state, a R-phase, a composite state between martensitic and R-phase, etc.) and a second material phase or state (e.g., an austenitic state, an R-phase state, a composite state between austenitic and R-phase, etc.). In the first material state, the first actuation element $126a_1$ and the second actuation element $126a_2$ may have reduced (e.g., relatively less stiff) mechanical properties that cause the actuation elements to be more easily deformable (e.g., compressible, expandable, etc.) relative to when the actuation elements are in the first material state. In the second material state, the first actuation element $126a_1$ and the second actuation element $126a_2$ may have increased (e.g., relatively more stiff) mechanical properties relative to the first material state, causing an increased preference toward a specific preferred geometry (e.g., original geometry, manufactured or fabricated geometry, heat set geometry, etc.). The first actuation element $126a_1$ and the second actuation element $126a_2$ can be selectively and independently transitioned between the first material gate and the second material gate by applying energy (e.g., laser energy, heat, electrical energy, etc.) to the first actuation element $126a_1$ or the second actuation element $126a_2$ to heat it above a transition temperature.

The first actuation element $126a_1$ and the second actuation element $126a_2$ generally act in opposition. For example, the first actuation element $126a_1$ can be actuated to move the first gating element 124a toward the closed position, and the second actuation element $126a_2$ can be actuated to move the first gating element 124a toward the open position. Additionally, the first actuation element $126a_1$ and the second actuation element $126a_2$ are coupled such that as one moves toward its preferred geometry upon material phase transition, the other is deformed relative to its preferred geometry. This enables the actuation elements to be repeatedly actuated and the first gating element 124a to be repeatedly cycled between the open position and the closed position. The second actuator 122b and the third actuator 122c can also each include a pair of opposing shape-memory actuators and operate in the same or similar fashion as the first actuator 122a. Additional details regarding the operation of shape memory actuators, as well as adjustable glaucoma shunts, are described in U.S. Patent App. Publication Nos. 2020/0229982 and 2021/0251806, and International Patent Application Nos. PCT/US2020/055144 and PCT/US2020/055141, the disclosures of which are incorporated by reference herein in their entireties and for all purposes. Additional details of the plate assembly 120 are described with respect to FIGS. 2A-4D.

In operation, the system 100 can be used to drain aqueous from the anterior chamber of the eye to treat glaucoma. Accordingly, when the system 100 is implanted in an eye to treat glaucoma, the first end portion 102a of the elongated housing 102 can be positioned within an anterior chamber of the patient's eye such that the fluid inlets 104 are in fluid communication with the anterior chamber, and the second end portion 102b can be positioned in a target outflow location, such as a subconjunctival bleb space, such that the fluid outlets 106 are in fluid communication with the target outflow location. As described in greater detail below, aqueous can flow into the elongated housing via the fluid inlets 104, through the plate assembly 120, into the main fluid conduit 110, and exit via the fluid outlets 106.

As described in more detail below, the relative level of therapy provided by each fluid inlet 104 can be different so that a user may selectively control the flow through the system 100 by selectively interfering with or permitting flow through individual fluid inlets 104. For example, under a given pressure, when flow primarily occurs through the first fluid inlet 104a, the system 100 can provide a first drainage rate, when flow primarily occurs through the second fluid inlet 104b, the system 100 can provide a second drainage rate greater than the first drainage rate, and when flow primarily occurs through the third fluid inlet 104c, the system 100 can provide third drainage rate greater than the first drainage rate. The foregoing difference in drainage rates can be achieved by varying the fluid resistance of channels (e.g., channels 254a-c, shown in FIGS. 2A-2D) receiving fluid from the respective inlets 104a-c.

Figure 2A:
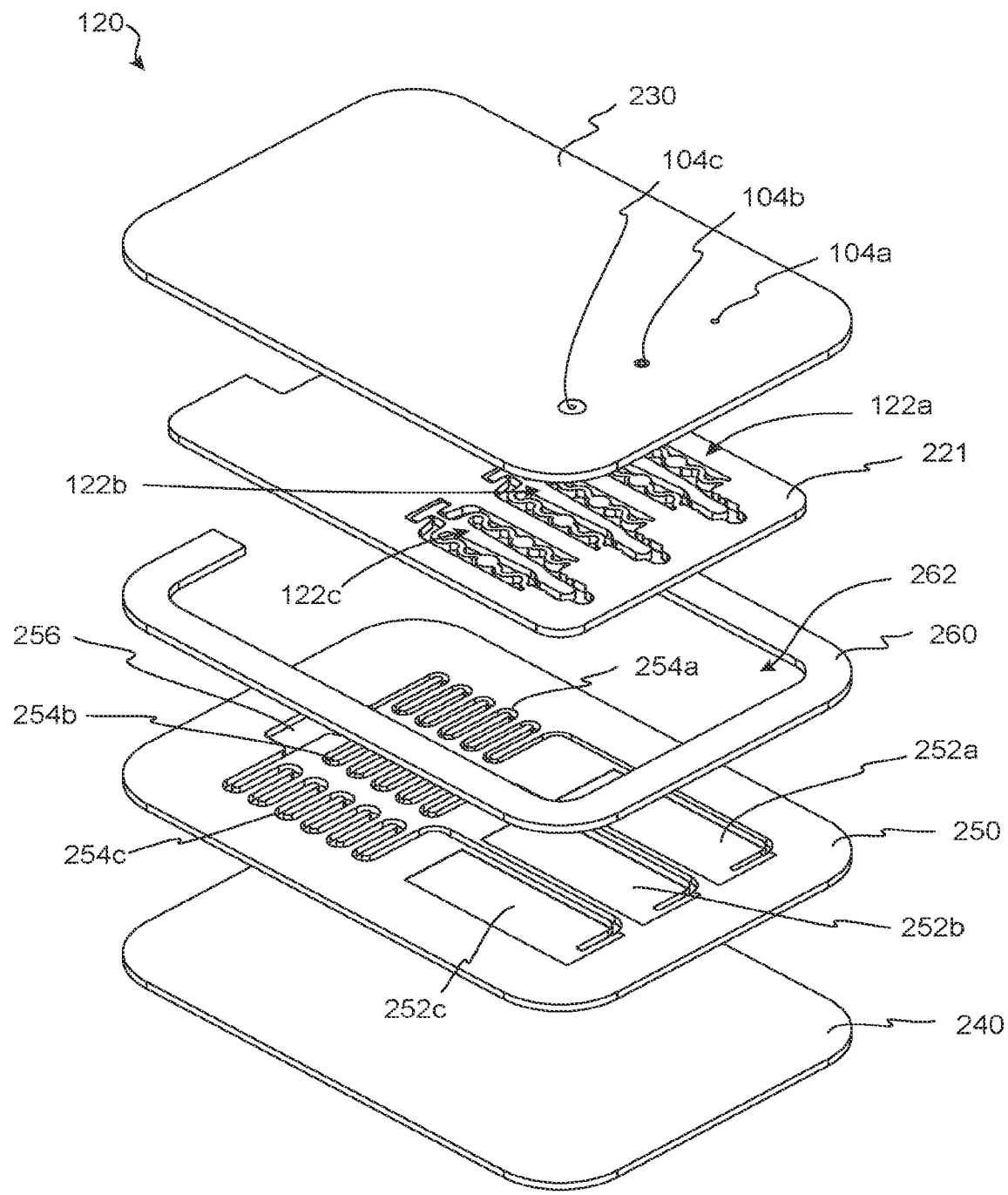
FIGS. 2A-2D illustrate a plate assembly for use with an intraocular shunting system and configured in accordance with select embodiments of the present technology.
Figure 2B:
Figure 2C:
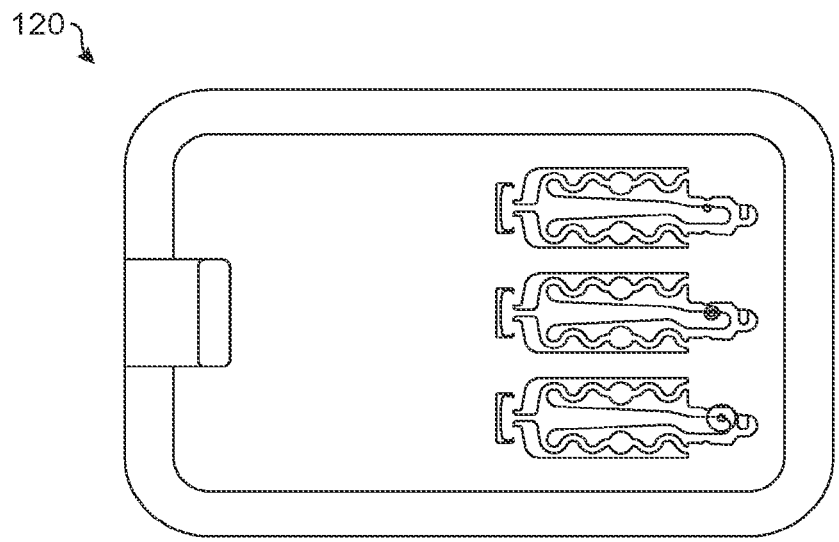

Although described as having three inlets 104 and three actuators 122, the plate assembly 120 can have more or fewer inlets 104 and actuators 122. For example, the plate assembly 120 can have one, two, four, five, six, or M ore inlets 104 and actuators 122, FIGS. 2A-2D illustrate the plate assembly 120 with other aspects of the system 100 omitted for clarity. In particular, FIG. 2A is an exploded view of the plate assembly 120, FIG. 2B is a side view of the plate assembly 120, FIG. 2C is a top down view of the plate assembly 120, and FIG. 21) is a bottom up view of the plate assembly 120. Referring first to FIG. 2A, the plate assembly 120 includes an actuation assembly 221 and a plurality of discrete layers or sheets, including a first (e.g., top) sheet 230, a second (e.g., bottom) sheet 240, a third (e.g., middle) sheet 250, and a fourth (e.g., spacer) sheet 260 (collectively referred to as the "sheets 230-260"). The actuation assembly 221 includes the first actuator 122a, the second actuator 122b, and the third actuator 122c, described above with respect to FIG. 1. In some embodiments, the actuation assembly 221 is formed as a single piece of material such that the first actuator 122a, the second actuator 122b, and the third actuator 122c are a contiguous unitary element. Despite being a contiguous unitary element, the actuation elements 126 can still operate substantially independently of one another. The actuation assembly 221 can be produced via a photolithographic process, via a deposition process, via cutting or etching a unitary structure from a sheet or source material, or other suitable techniques for forming shape memory materials.

The sheets 230-260 are configured to stack atop, adhere to, or be adhered to one another, e.g., to form a cartridge. In particular, an upper surface of the second sheet 240 is configured to engage and adhere to a lower surface of the third sheet 250, an upper surface of the third sheet 250 is configured to engage and adhere to a lower surface of the fourth sheet 260, and an upper surface of the fourth sheet 260 is configured to engage and adhere to a lower surface of the first sheet 230. When the sheets 230-260 are stacked atop and adhered to one another, the boundaries between adjacent sheets of the sheets 230-260 are or can be fluidically sealed to prevent fluid from leaking into or out of the plate assembly. The sheets 230-260 can be adhered through any suitable technique, including gluing, welding, soldering, bonding, or the like. In some embodiments, the sheets 230-260 are self-bonding and automatically adhere to one another if placed un der certain conditions (e.g. in a vacuum). In some embodiments, rather than adhering the sheets 230-260 to one another, the sheets 230-260 are placed within a case or other membrane that holds the sheets 230-260 in the desired orientation. In such embodiments, the gaps between adjacent sheets can be partially or fully sealed using a sealant to prevent unwanted fluid leakage between adjacent sheets.

The sheets 230-260 encompass the actuation assembly 221. For example, the fourth sheet 260 defines an outer frame with an empty interior 262 that is sized and shaped to receive the actuation assembly 221. Accordingly, when the sheets 230-260 are stacked atop and adhered to one another, the actuation assembly 221 sits within the empty interior 262 of the fourth sheet 260 (e.g., the fourth sheet 260 at least partially encircles a lateral boundary of the actuation assembly 221) and between the third sheet 250 and the first sheet 230. One or more of the sheets 230-260 can be composed of a transparent material. That way, light (e.g. laser) energy can be applied to actuate (e.g., heat) the actuators 122 even when the actuation assembly 221 is fully enclosed within the sheets 230-260. For example, in some embodiments, the first sheet 230 is composed of quartz (e.g., silicon dioxide), glass, alumina (sapphire) metals (e.g., Si, Pt, Au, etc.), plastic, and/or other suitable material, and a user directs laser energy through the first sheet 230 to one or more actuators 122. In some embodiments, all of the sheets 230-260 are composed of the same material (e.g., glass). In some embodiments, the material is substantially rigid. In some embodiments, the first sheet 230 may not be fully transparent, but instead may include one or more transparent windows aligned with the actuators 122.

The first sheet 230 includes the fluid inlets 104a-c. As described above, the fluid inlets 104a-c permit fluid to enter the plate assembly 120, and the actuators 122 can control the flow of fluid through the fluid inlets 104. The third sheet 250 includes a first cavity or depression 252a, a second cavity or depression 252b, and a third cavity or depression 252c (collectively referred to herein as the "cavities 252"). The upper surface of the cavities 252 can be slightly recessed relative to the upper surface of the third sheet 250 and are configured to align with the first actuator 122a and/or the first fluid inlet 104a, the second actuator 122b and/or the second fluid inlet 104b, and the third actuator 122c and/or the third fluid inlet 104c. Aligning the first actuator 122a, the second actuator 122b, and the third actuator 122c with the first cavity 252a, the second cavity 252b, and the third cavity 252c, respectively, prevents the upper surface of the third sheet 250 from interfering with (e.g., preventing movement of) the actuators 122. For example, a small gap can exist between at least a portion of the actuators 122 (e.g., the actuation elements and/or gating element) and the third sheet 250. In some embodiments, the cavities 252 only exist under the moveable portions of the actuators 122 (e.g., the actuation elements and gating elements). Furthermore, the first cavity 252a can collect fluid entering the plate assembly 120 via the first fluid inlet 104a, the second cavity 252b can collect fluid entering the plate assembly 120 via the second fluid inlet 104b, and the third cavity 252c can collect fluid entering the plate assembly 120 via the third fluid inlet 104c. The cavities 252 can be substantially fluidly isolated to provide greater control of the level of therapy provided by the system, as described in greater detail below.

The third sheet 250 also includes channels 254 for draining fluid through the plate assembly 120. In particular, the third sheet 250 includes a first channel 254a in fluid communication with the first cavity 252a, a second channel 254b in fluid communication with the second cavity 252b, and a third channel 254c in fluid communication with the third cavity 252c. Each of the channels 254 terminate in a fluid collection well 256 that can be fluidly coupled to or otherwise drain into the main fluid conduit(s) 110 of the elongated housing 102. Accordingly, in the embodiment shown in FIGS. 1-2D, the actuation assembly 221 is encircled by a different sheet or layer (i.e., the fourth sheet 260) than the sheet or layer that defines the channels 254 (i.e., the third sheet 250).

As described above, fluid draining via the system 100 travels through the plate assembly 120 (and thus at least one of the channels 254). If the first actuator 122a is in the open position, fluid entering the plate assembly 120 via the first fluid inlet 104a (FIG. 1) can flow into the first cavity 252a of the plate assembly 120. The fluid then drains from the first cavity 252a to the manifold 111, and thus the main fluid conduit 110, via the first channel 254a. Likewise, if the second actuator 122b is in the open position, fluid entering the plate assembly 120 via the second fluid inlet 104b (FIG. 1) can flow into the second cavity 252b of the plate assembly 120. The fluid then drains from the second cavity 252b to the manifold 111, and thus the main fluid conduit 110, via the second channel 254b. If the third actuator 122c is in the open position, fluid entering the plate assembly 120 via the third fluid inlet 104c (FIG. 1) can flow into the third cavity 252c of the plate assembly 120. The fluid then drains from the third cavity 252c to the manifold 111, and thus the main fluid conduit 110, via the third channel 254c.

The channels 254 can have different dimensions (e.g., length, width, height, cross-section area, etc.) such that each channel 254 provides a different resistance to flow. For example, the first channel 254a can provide a first resistance, the second channel 254b can provide a second resistance less than the first resistance, and the third channel 254c can provide a third resistance less than the second resistance. The therapy level (e.g., drainage rate of aqueous) provided by the system 100 can therefore be controlled by selectively controlling which route(s) through the plate assembly 120 are open to fluid flow. For example, to provide a first relatively small level of therapy, the first actuator 122a can be in an open position while the second actuator 122b and the third actuator 122c are in a closed position. Thus, the only route for fluid to drain through the system 100 is through the first channel 254a, which, as described above, has a relatively high resistance to flow. Thus, the drainage rate is relatively low. To provide a second relatively higher level of therapy, the third actuator 122c can be in an open position while the second actuator 122b and the first actuator 122a are in a closed position. Thus, the only route for fluid to drain through the system 100 is through the third channel 254c, which, as described above, has a relatively low resistance to flow. Thus, the drainage rate is relatively high. Of course, the actuators 122 can be selectively positioned at any combination of open and closed positions to provide the desired level of therapy. Additional details regarding providing multiple discrete therapy levels using shunting systems having a variety of fluid inlets and flow channels are described in International Patent Publication No. WO2021/151007, the disclosure of which is incorporated by reference herein in its entirety.

Figure 2D:
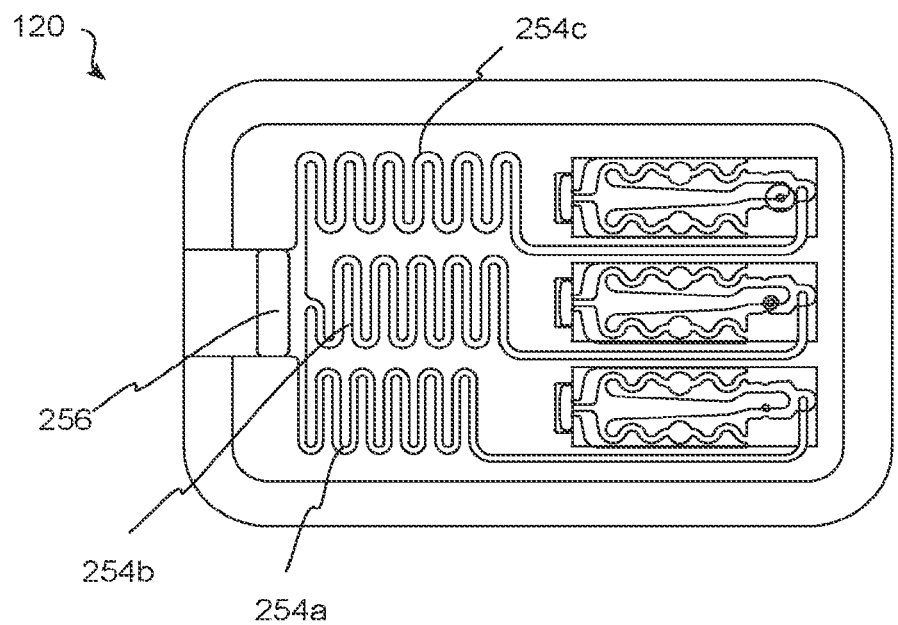

FIG. 2B provides a side view of the plate assembly 120 in an assembled or stacked configuration and illustrates the relative orientation of the sheets 230-260. The actuation assembly 221 cannot be seen in the side view because, as described above, it sits within the empty interior 262 of the plate assembly 120 defined by the fourth sheet 260. FIG. 2C provides a top down view of the plate assembly 120. The channels 254 cannot be seen because the actuation assembly 221 is not transparent and sits on top of the third sheet 250 that has the channels 254. FIG. 2D provides a bottom up view of the plate assembly 120.

Figure 3A:
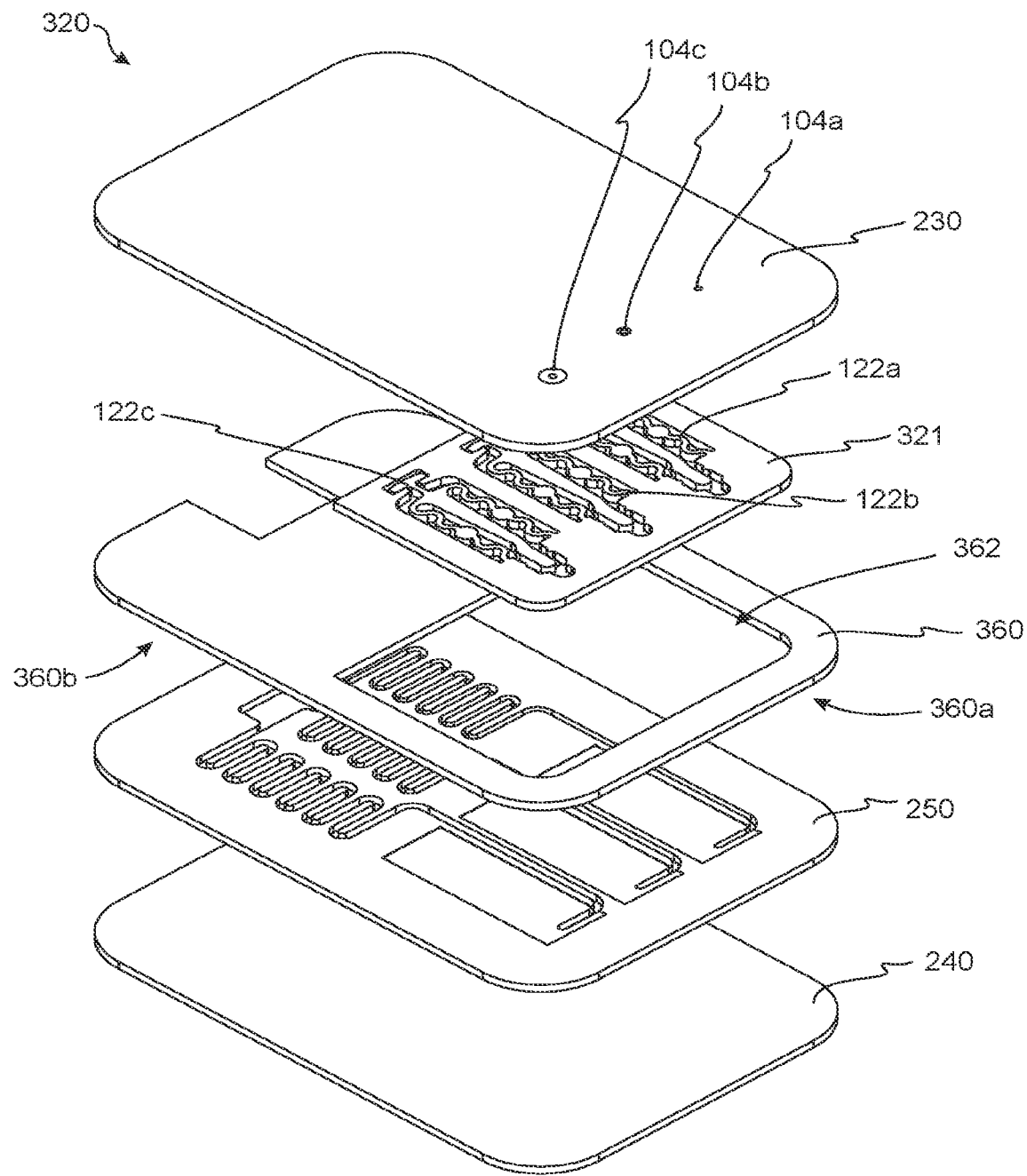
FIGS. 3A-3C illustrate another plate assembly for use with an intraocular shunting system and configured in accordance with select embodiments of the present technology.
Figure 3B:
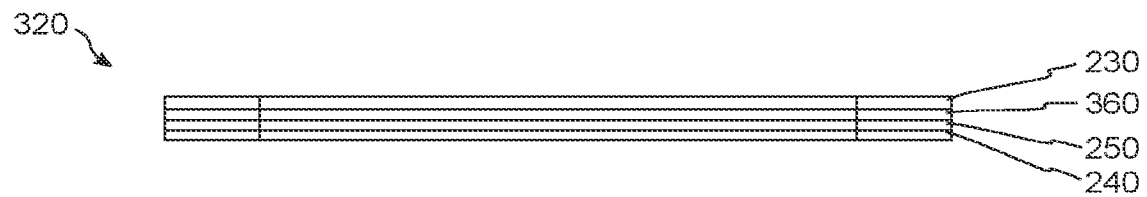
Figure 3C:
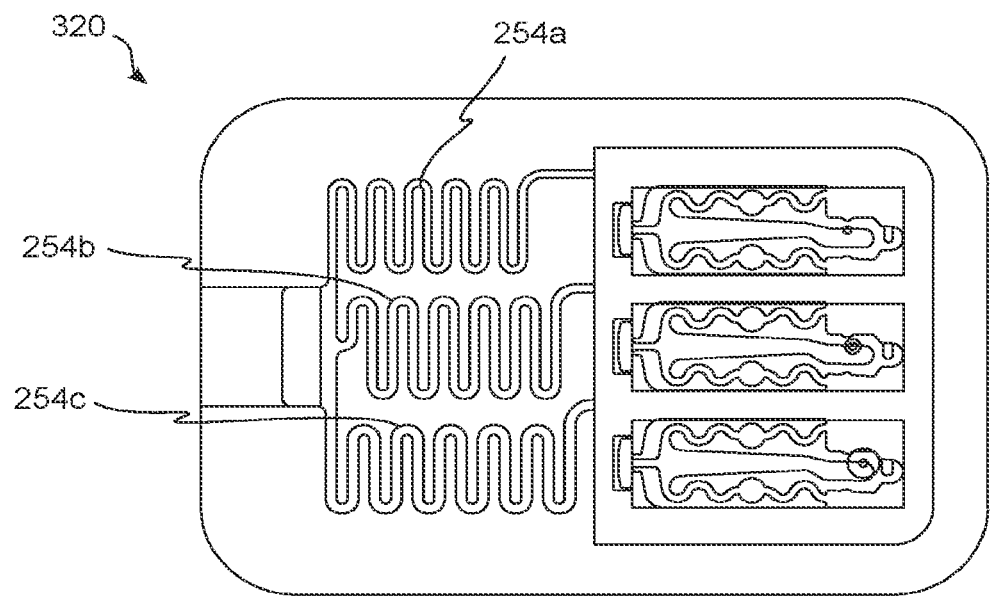

FIGS. 3A-3C illustrate a plate assembly 320 slightly modified relative to the plate assembly 120 (FIG. 1) and configured in accordance with select embodiments of the present technology. In particular, FIG. 3A is an exploded view of the plate assembly 320, FIG. 3B is a side view of the plate assembly 320, and FIG. 3C is a top down view of the plate assembly 320. The plate assembly 320 is generally similar to the plate assembly 120, and can be used with the system 100 instead of the plate assembly 120 to control the flow of fluid therethrough. Relative to the plate assembly 120, the plate assembly 320 includes an actuation assembly 321 that is sized to only extend along a portion of a length of the plate assembly 320. For example, a length of the actuation assembly 321 is less than about three-quarters, less than about one-half, or less than about one-third the length of the first sheet 230. This requires use of less shape-memory material while manufacturing the actuation assembly 321, without substantially impacting the performance of the actuators 122. To accommodate the smaller actuation assembly 321, a fourth sheet 360 has an empty space 362 at a first end region 360a sized and shaped to receive (e.g., snuggly receive) the actuation assembly 321. Unlike the fourth sheet 160, a second end region 360b does not have an empty space, but rather is a solid structure.

The plate assembly 320 still forms an enclosed cartridge, with the first sheet 230, the second sheet 240, the third sheet 250, and the fourth sheet 360 enclosing the actuation assembly 321, as best shown in FIG. 3B. However, because the actuation assembly 321 does not extend the substantially full length of the plate assembly 320, the channels 254 can be seen both when looking down on the plate assembly 320, as best shown in FIG. 3C., and when looking up at the plate assembly 320 (not shown) in embodiments in which each sheet is a transparent material such as glass or plastic.

Figure 4A:
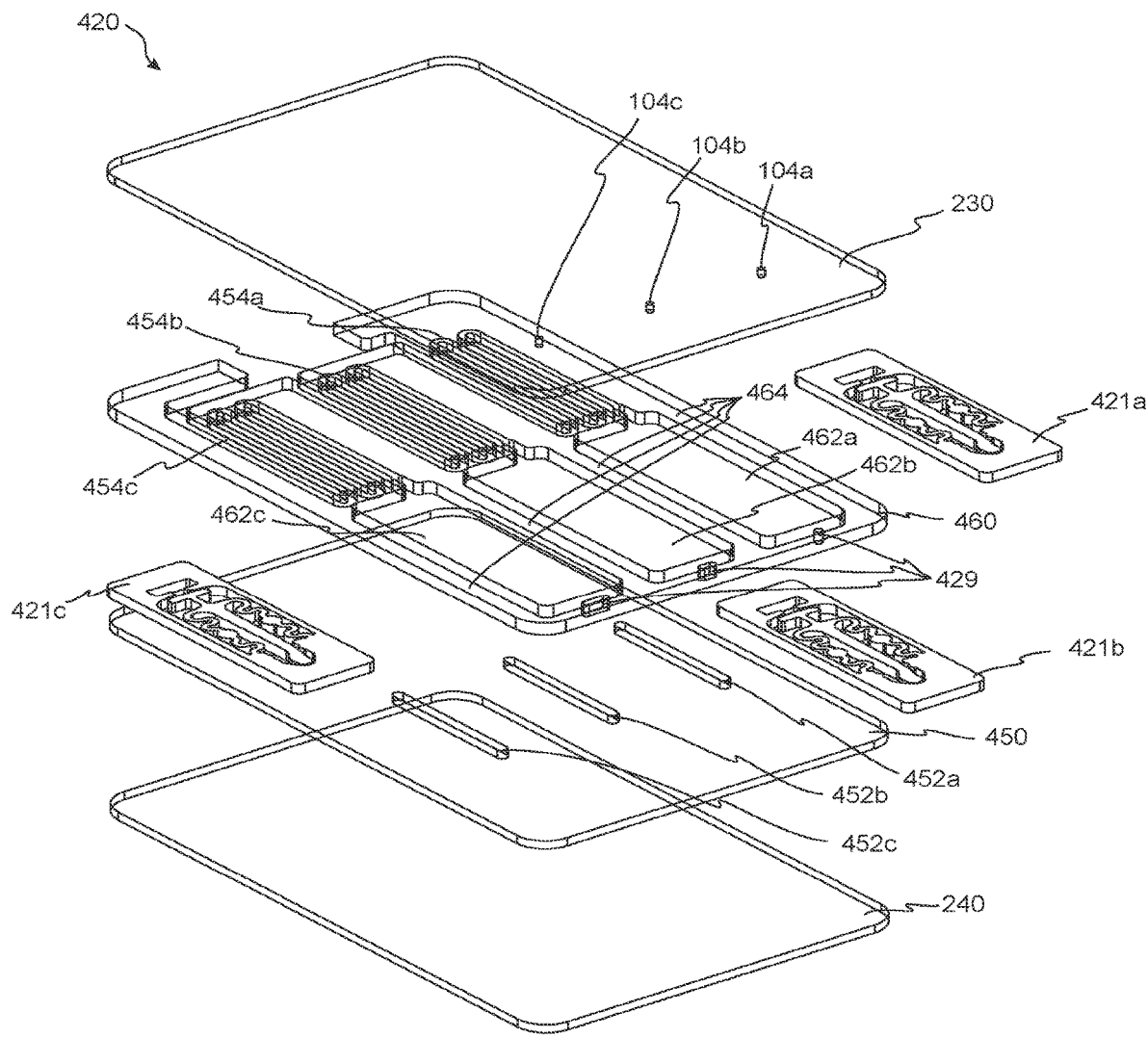
FIGS. 4A-4C illustrate another plate assembly for use with an intraocular shunting system and configured in accordance with select embodiments of the present technology.
Figure 4B:
Figure 4C:
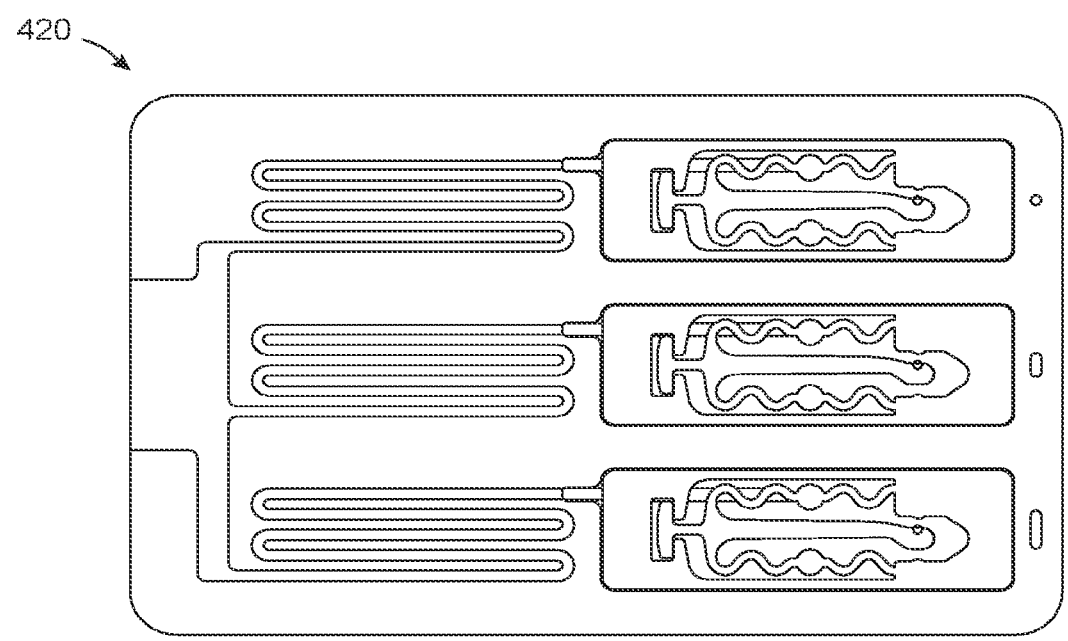

FIGS. 4A-4C illustrate another plate assembly 420 slightly modified relative to the plate assembly 120 (FIG. 1) and configured in accordance with select embodiments of the present technology. In particular, FIG. 4A is an exploded view of the plate assembly 420, FIG. 4B is a side view of the plate assembly 420, and FIG. 4C is a top down view of the plate assembly 420. The plate assembly 420 is generally similar to the plate assembly 120, and can be used with the system 100 instead of the plate assembly 120 to control the flow of fluid therethrough. Relative to the plate assembly 120, the plate assembly 420 of FIGS. 4A-4C includes three discrete actuation assemblies: a first actuation assembly 421a, a second actuation assembly 421b, and a third actuation assembly 421c (collectively referred to herein as "the actuation assemblies 421"). This is opposed to the plate assembly 120, in which the actuation assembly 221 is a single contiguous element. To accommodate the three discrete actuation assemblies 421, a fourth sheet 460 is structured to define a first empty space 462a for receiving the first actuation assembly 421a, a second empty space 462b for receiving the second actuation assembly 421b, and a third empty space 462c for receiving the third actuation assembly 421c. Accordingly, the actuation assemblies 421 are separated by segments 464 of the fourth sheet 460 that define the empty spaces 462. When the fourth sheet 460 is adhered to the first sheet 230 and the third sheet 450, the segments 464 also adhere to the first sheet 230 and the third sheet 450, creating individual compartments for the actuation assemblies 421 to reside within. Because the sheets are made of a rigid material (e.g., glass), the individual compartments are structurally stiffer than the actuation assemblies 421, and therefore isolate the actuation assemblies 421 such that operation of one of the actuation assemblies 421 does not substantially affect or deform another actuation assembly 421.

Furthermore, unlike the plate assemblies 120 and 320, the fourth sheet 460 of the plate assembly includes a first channel 454a, a second channel 454b, and a third channel 454c (collectively referred to herein as the "channels 454"), each of which can have different fluid resistances. Thus, in the embodiment shown in FIGS. 4A-4C, the same layer or sheet both (1) encircles/houses the actuation assemblies 421 and (2) defines the channels 454. Despite being positioned in the fourth sheet 460, the channels 454 can operate in a substantially similar manner as the channels 254 of the plate assemblies 120 and 320. For example, the channels 454 can transport fluid through the plate assembly 420 to aid in draining fluid from a first body region. In some embodiments, the fourth sheet 460 can include visualization features 429 that correspond to the relative level of resistance through each channel 454 (e.g., a first mark denotes the corresponding channel has the highest resistance, a second mark denotes the corresponding channel has the lowest resistance, etc.). This can help a user determine which inlets 104 to open or close to achieve a desired therapeutic outcome.

The plate assembly 420 also includes a third sheet 450 that includes elongated depressions or wells 452 (e.g., a first depression 452a, a second depression 452b, and a third depression 452c). The depressions 452 can collect fluid entering via the inlets 104a-c to transport the fluid to the respective channels 454a-c to permit fluid to flow between the inlet 104 and the corresponding channel 454, e.g., when the corresponding actuation assembly 421 is in an open position. The depressions 452 accordingly form a channel-like path that fluid flows through the fluid flows through the plate assembly 420. The depressions 452 can therefore also be referred to as defining a "first portion" of the corresponding channels 454, rather than as separate features (e.g., the first depression 452a and the first channel 454a collectively form a first elongated flow channel, the second depression 452b and the second channel 454b collectively form a second elongated flow channel, etc.). In some embodiments, the third sheet 450 may be omitted from the plate assembly 420, and fluid can flow around the actuation assembly but within the empty space 462 to reach the channel 454.

As with the plate assemblies 120 and 320, the plate assembly 420 still forms an enclosed cartridge, with the first sheet 130, the second sheet 140, the third sheet 450, and the fourth sheet 460 enclosing the actuation assemblies 421, as best shown in FIG. 4B. Similar to the plate assembly 320, the channels 454 can be seen both when looking down on the plate assembly 420 (as best shown in FIG. 4C) and when looking up at the plate assembly 420.

As one skilled in the art will appreciate, any of the plate assemblies described above can be used with the system 100 to control the flow of fluid therethrough. Moreover, certain features described with respect to one plate assembly can be added or combined with another plate assembly. Accordingly, the present technology is not limited to the plate assemblies expressly identified herein.

Incorporating a plate assembly such as those described above into adjustable shunting systems is expected to provide several advantages. For example, many of the components required to produce an adjustable shunting system capable of providing a titratable and adjustable therapy are very small and difficult to manufacture using conventional techniques for molding plastic, steel, or other non-transparent materials. In contrast, utilizing the plate assemblies described herein is expected to reduce the complexity of manufacturing. For example, the sheets of the plate assembly (e.g., the sheets 230-260 of the plate assembly 120) can be formed via known techniques for fabricating transparent materials that have a relatively high resolution (e.g., about 10 microns or less) and high reproducibility. In some embodiments, the sheets are formed using additive manufacturing processes with submicron resolution. Such techniques tend to have greater resolution than techniques for cutting nitinol, non-transparent plastics, steel, and other non-transparent materials, permitting greater control over the shape and flow characteristics of the plate assembly (e.g., providing eater control over the dimensions of the channels 254, etc.).

Another expected advantage is that in at least some embodiments, the plate assemblies or features thereof can be manufactured in bulk. For example, hundreds or even thousands of copies of a single component of the plate assembly (e.g., the first sheet can be etched or otherwise fabricated in a first disc or sheet of material. Copies of a second component (e.g., the second sheet of the plate assembly) can be etched or otherwise fabricated in a second disc or sheet of material, copies of a third component (e.g., the third sheet) can be etched or otherwise fabricated in a third disc or sheet of material, and so on. The discs or sheets of material can then be stacked such that individual first components align with individual second components, individual third components, and so on. The discs or other sheets of material can then be bonded or otherwise adhered, forming a plurality of plate assemblies. The formed plate assemblies can then simply be cut from the disc or other sheet of material in bulk, producing hundreds or even thousands of the plate assemblies. In some embodiments, these manufacturing techniques can be generally similar to fabrication techniques used to make integrated circuits and micro-electromechanical devices.

The present technology may provide additional advantages beyond those explicitly described above. For example, the present technology may provide enhanced surface quality for the plate assemblies and/or shunting systems, better mechanical properties of the plate assemblies and/or shunting systems, and/or enable a larger selection of materials to be used for fabricating the plate assemblies and/or shunting systems.

Figure 5:
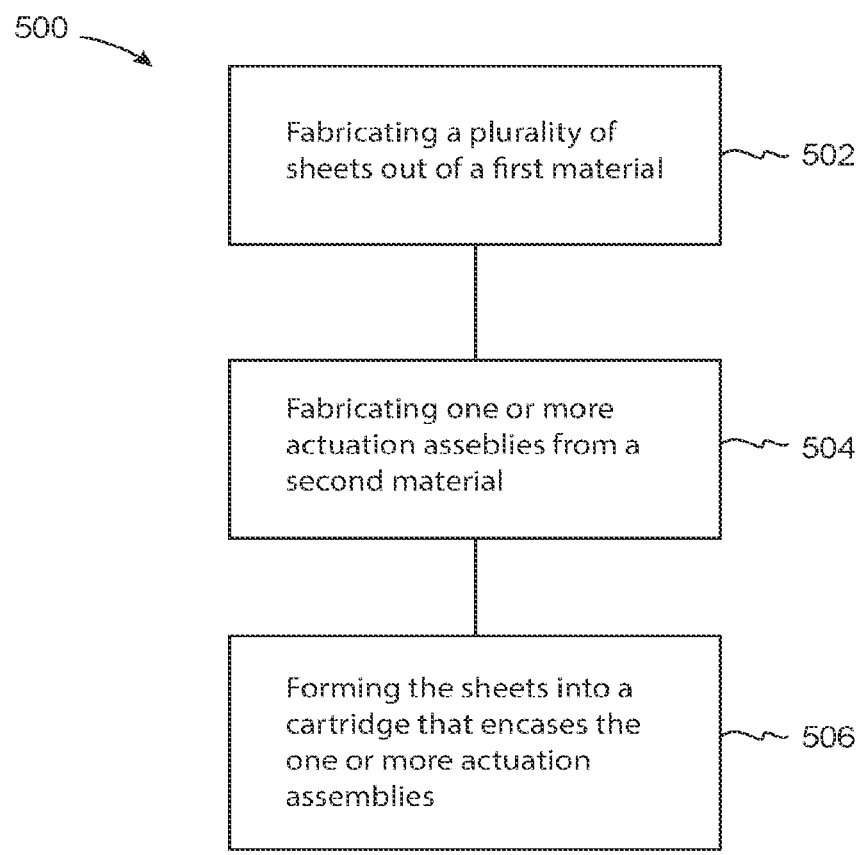
FIG. 5 is a flowchart of a method form manufacturing a plate assembly in accordance with select embodiments of the present technology.

The present technology further includes methods of manufacturing the plate assemblies described herein. For example, FIG. 5 is a flowchart of a method 500 for making a plate assembly in accordance with embodiments of the present technology. The method 500 can begin at step 502 by fabricating a plurality of sheets from a first material. This can include, for example, forming a first (e.g., upper) sheet, a second (e.g., lower) sheet, a third (e.g., middle) sheet, and a fourth (e.g., spacer) sheet. The sheets can be formed out of a transparent and rigid material, such as glass, and may be formed via any suitable process having a relatively high resolution (e.g., 3D printing). The sheets may be formed with certain features described above, such as channels, cavities, apertures, and the like.

The method 500 can continue at step 504 by fabricating one or more actuation assemblies from a second material. This can include, for example, fabricating the one or more actuation assemblies from nitinol or another shape memory material via a photolithographic process, via a deposition process, via cutting or etching a unitary structure from a sheet or source material, or other suitable techniques for forming shape memory materials. In some embodiments, a single unitary actuation assembly is formed at step 504. In other embodiments, multiple discrete actuation assemblies are formed at step 504.

The method 500 can continue at step 506 by forming or assembling the sheets into a cartridge that encases the one or more actuation assemblies (e.g., thereby forming the plate assembly). This can be done by stacking the plates on top of one another and adhering adjacent plates to one another. In some embodiments, this includes gluing, welding, soldering, bonding or otherwise securing adjacent plates to one another. In some embodiments, this includes placing the sheets into a vacuum such that the sheets automatically self-bond to one another. The formed plate assembly can then optionally be positioned within an elongated housing to font a shunting system.

Figure 6:
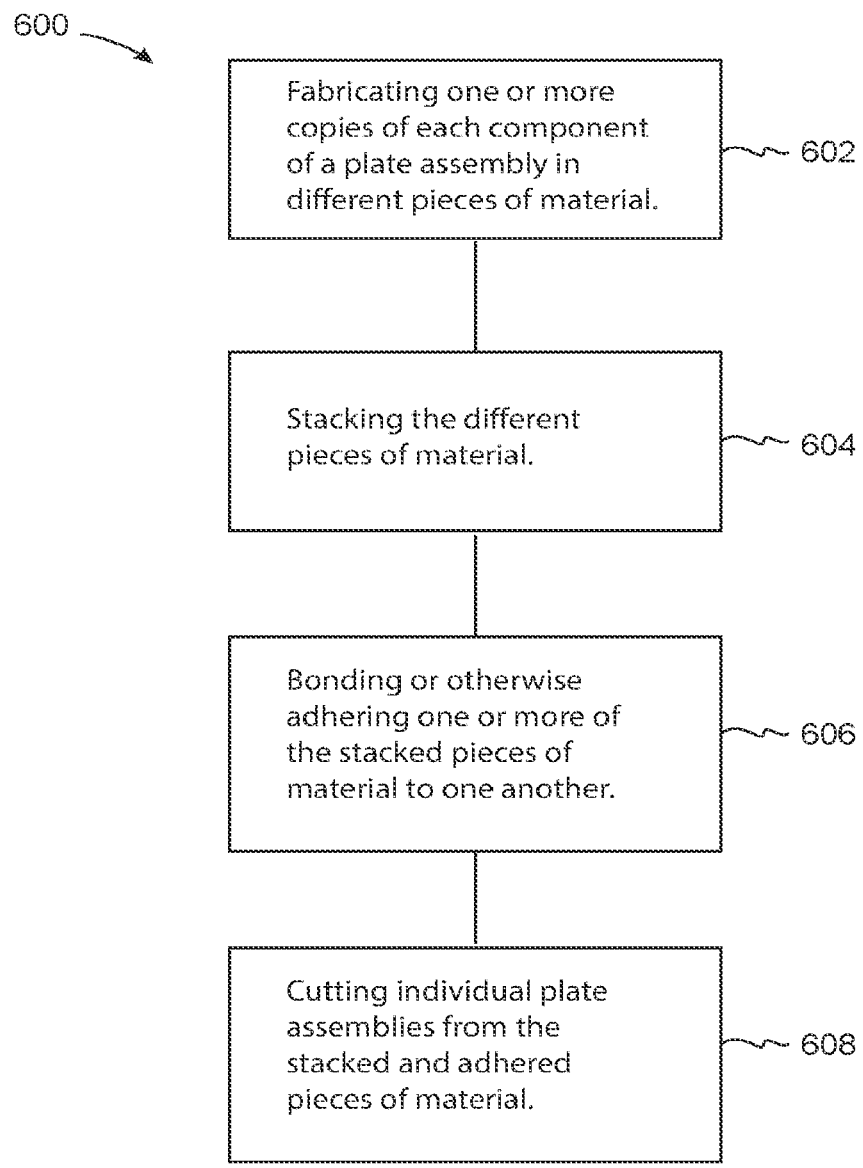
FIG. 6 is a flowchart of a method for manufacturing plate assemblies in accordance with select embodiments of the present technology.

FIG. 6 is a flowchart of a method 600 for fabricating the plate assemblies described herein in bulk. The method 600 can begin at step 602 by fabricating one or more copies of each component of a plate assembly in different pieces of material. This may include, for example, fabricating multiple copies of a first component of the plate assembly (e.g., a first sheet) in a first piece of material, fabricating multiple copies of a second component of the plate assembly (e.g., a second sheet) in a second piece of material, fabricating copies of a third component of the plate assembly (e.g., a third sheet) in a third piece of material, fabricating multiple copies of a fourth component of the plate assembly (e.g., a fourth sheet) in a fourth piece of material, and/or fabricating multiple copies of a fifth component of the plate assembly (e.g., the actuation assemblies) in a fifth piece of material. In some embodiments, fabricating multiple copies includes fabricating hundreds or thousands of copies of each component in their respective pieces of material.

The method 600 can continue at step 604 by stacking the pieces of material on top of one another such that individual first components of the first piece of material align with individual second components of second piece of material, individual second components of the second piece of material align with individual third components of the third piece of material, individual third components of the third piece of material align with individual fourth components of the fourth piece of material, and individual fourth components of the fourth piece of material align with individual fifth components of the fifth piece of material. Of course, the pieces of material can be stacked in the order corresponding to the desired layered arrangement for the plate assembly.

The method 600 can continue at step 606 by bonding or otherwise adhering one or more of the stacked pieces of material to one another. This can include, for example, exposing the stacked pieces of material to a vacuum such that one or more of the stacked pieces automatically self-bond. In other embodiments, one or more of the stacked pieces of material can be glued or otherwise adhered together.

The method 600 can continue at step 608 by cutting individual plate assemblies from the stacked and adhered pieces of material. In some embodiments, hundreds or even thousands of plate assemblies can be cut from the stacked and adhered pieces of material.

EXAMPLES

Several aspects of the present technology are set forth in the following examples:

1. A flow control plate for use with a shunting system for treating a patient, the flow control plate comprising:
    a shape memory actuation assembly having one or more actuators configured to control the flow of fluid through the flow control plate;
    a first sheet forming a top structure of the flow control plate, wherein the first sheet includes one or more fluid inflow apertures;
    a second sheet forming a bottom structure of the flow control plate; and
    one or more intermediate sheets positioned between the first sheet and the second sheet, wherein the one or more intermediate sheets encircle a lateral boundary of the shape memory actuation assembly, and wherein the one or more intermediate sheets at least partially define one or more channels configured to receive fluid from the one or more fluid inflow apertures.
2. The flow control plate of example 1 wherein the one or more intermediate sheets include:
    a third sheet at east partially defining the one or more channels configured to receive fluid from the one or more fluid inflow apertures; and
    a fourth sheet encircling the lateral boundary of the actuation assembly.
3. The flow control plate of example 2 wherein the third sheet further includes a cavity aligned with the actuation assembly such that at least a portion of a lower surface of the actuation assembly does not contact the third sheet.
4. The flow control plate of example 1 wherein the one or more intermediate sheets include a third sheet having (i) the one or more channels configured to receive fluid from the one or more fluid inflow apertures, and (ii) a chamber or empty space configured to receive the shape memory actuation assembly and encircle a lateral boundary of the shape memory actuation assembly.
5. The flow control plate of example 4 wherein the one or more intermediate sheets include a fourth sheet positioned between the second sheet and the third sheet, wherein the fourth sheet includes one or more depressions configured to align with and extend between the chamber or empty space and at least one of the one or more channels.
6. The flow control plate of any of examples 1-5 wherein the first sheet, the second sheet, and the one or more intermediate sheets are composed of quartz and or glass.
7. The flow control plate of any of examples 1-6 wherein the shape memory actuation assembly is composed of nitinol.
8. The flow control plate of any of examples 1-7 wherein the shape memory actuation assembly is a first shape memory actuation assembly, the flow control plate further including a second shape memory actuation assembly distinct from the first shape memory actuation assembly.
9. The flow control plate of example 8 wherein the one or more intermediate sheets include a third sheet having a first chamber configured to house the first actuation assembly and a second chamber configured to house the second actuation assembly, and wherein the first chamber is fluidly isolated from the second chamber.

10. The flow control plate of any of examples 1-9 wherein each of the first sheet, the second sheet, and the one or more intermediate sheets are adhered to at least one of the first sheet, the second sheet, or the one or more intermediate sheets.

11. The flow control plate of any of examples 1-10 wherein the first sheet, the second sheet, and the one or more intermediate sheets have a stacked configuration, and wherein the first sheet, the second sheet, and the one or more intermediate sheets form a fluid seal such that fluid cannot leak between the first sheet, the second sheet, and the one or more intermediate sheets.

12. A layered flow control plate for use with a shunting system for treating a patient the layered flow control plate including:
   a plurality of layers defining a fluid flow path including (a) one or more apertures, and (b) one or more channels configured for fluid communication with the one or more apertures; and
   a shape memory actuation assembly having one or more actuators configured to control the flow of fluid through the fluid flow path, wherein the shape memory actuation assembly is encased within the plurality of layers.

13. The layered flow control plate of example 12 wherein a common layer of the plurality of layers forms a lateral boundary around the shape memory actuation assembly and defines the one or more channels.

14. The layered flow control plate of example 12 wherein a first layer of the plurality of layers forms a lateral boundary around the shape memory actuation assembly, and wherein a second layer of the plurality of layers defines the one or more channels, the first layer being different than the second layer.

15. The layered flow control plate of any of examples 12-14 wherein the plurality of layers includes at least a first layer and a second layer, and wherein the first layer defines a first portion of the one or more channels and the second layer defines a second portion of the one or more channels.

16. The layered flow control plate of any of examples 12-15 wherein the plurality of layers includes:
   a first layer forming a first outer surface of the flow control plate,
   a second layer forming a second outer surface of the flow control plate, and
   one or more intermediate layers, wherein the one or more intermediate layers define the one or more channels and form a lateral boundary around the shape memory actuation assembly.

17. A method of manufacturing a flow control plate having a shape memory actuation assembly and for use with a shunting system for treating a patient, the method comprising:
   fabricating a plurality of glass sheets, wherein the plurality of glass sheets includes (i) at least one glass sheet having one or more channels extending therethrough, and (ii) at least one Mass sheet defining an empty space configured to receive a shape memory actuation assembly; and
   assembling the flow control plate by forming the glass sheets into a cartridge that encase the shape memory actuation assembly within the empty space, wherein forming the glass sheets into the cartridge includes adhering adjacent glass sheets of the plurality of glass sheets to one another.

18. The method of example 17, further comprising fabricating the shape memory actuation assembly before assembling the flow control plate, wherein fabricating the shape memory actuation assembly includes fabricating the shape memory actuation assembly via a photolithographic process, via a deposition process, and/or via cutting or etching the shape memory actuation assembly from a sheet or source material.

19. The method of example 17 or example 18 wherein forming the glass sheets into the cartridge includes placing the glass sheets in a vacuum to automatically adhere adjacent glass sheets of the plurality of glass sheets together.

20. The method of any of examples 17-19 wherein fabricating the plurality of glass sheets includes fabricating:
   a first glass sheet configured to form the top of the cartridge;
   a second glass sheet configured to form the bottom of the cartridge;
   a third glass sheet defining the one or more channels; and
   a fourth glass sheet defining the empty space.

21. The method of any of examples 17-19 wherein fabricating the plurality of glass sheets includes fabricating:
   a first glass sheet configured to form the top of the cartridge;
   a second glass sheet configured to form the bottom of the cartridge;
   a third glass sheet defining the one or more channels and defining the empty space; and
   a fourth glass sheet having one or more depressions configured to align with the empty space and at least one of the one or more channels in the third glass sheet.

22. A method of manufacturing a flow control plate assembly for use with a shunting system for treating a patient, the method comprising:
   fabricating one or more copies of each component of the flow control plate assembly in different pieces of material;
   stacking the different pieces of material on top of one another such that individual components corresponding to individual flow control plate assemblies are aligned;
   bonding or otherwise adhering the stacked pieces of material to one another; and
   cutting individual flow control plate assemblies from the stacked and adhered pieces of material.

23. The method of example 22 wherein fabricating one or more copies of each component of the plate assembly in different pieces of material includes:
   fabricating multiple copies of a first component of the plate assembly in a first piece of material;
   fabricating multiple copies of a second component of the plate assembly in a second piece of material; and
   fabricating multiple copies of a third component of the plate assembly in a third piece of material.

24. The method of example 23 wherein stacking the pieces of material include stacking the first piece of material, the second piece of material, and the third piece of material such that individual first components are aligned with individual second components, and individual second components are aligned with individual first components.

25. The method of any of examples 22-24 wherein cutting individual plate assemblies from the stacked and adhered pieces of material include cutting more than 100 individual plate assemblies.
26. The method of any of examples 22-24 wherein cutting individual plate assemblies from the stacked and adhered pieces of material include cutting more than 1000 individual plate assemblies.

CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, any of the features of the intraocular shunts described herein may be combined with any of the features of the other intraocular shunts described herein and vice versa. Moreover, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions associated with intraocular shunts have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words "comprise," "comprising," and the like are to be construed in an inclusive sense, as opposed to an exclusive or exhaustive sense; that is to say, in the sense of "including but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A layered flow control plate for use with an implantable shunting system configured for treating a patient, the layered flow control plate including:
   a plurality of layers defining a fluid flow path including (a) one or more apertures, and (b) one or more channels configured for fluid communication with the one or more apertures; and
   a shape memory actuation assembly having one or more actuators configured to control the flow of fluid through the fluid flow path, wherein the shape memory actuation assembly is encased within the plurality of layers, wherein a first layer of the plurality of layers forms a lateral boundary around the shape memory actuation assembly, and wherein a second layer of the plurality of layers defines the one or more channels, the first layer being different than the second layer.

2. The layered flow control plate of claim 1, further comprising:
   a third layer forming a first outer surface of the flow control plate; and
   a fourth layer forming a second outer surface of the flow control plate.

3. The layered flow control plate of claim 2 wherein the first layer and the second layer are positioned between the third layer and the fourth layer.

4. The layered flow control plate of claim 1 wherein the second layer includes one or more cavities aligned with the actuation assembly such that a void exists under a portion of the actuation assembly.

5. The layered flow control plate of claim 1 wherein one or more of the plurality of layers are composed of quartz and/or glass.

6. The layered flow control plate of claim 1 wherein one or more of the plurality of layers are composed of a transparent material.

7. The layered flow control plate of claim 1 wherein at least the first layer is composed of a more rigid material than the shape memory actuation assembly.

8. The layered flow control plate of claim 1 wherein the shape memory actuation assembly is composed of nitinol.

9. The layered flow control plate of claim 1 wherein the shape memory actuation assembly is a first shape memory actuation assembly, and wherein the layered flow control plate further comprises a second shape memory actuation assembly distinct from the first shape memory actuation assembly.

10. The layered flow control plate of claim 9 wherein the first layer includes a first chamber configured to house the first actuation assembly and a second chamber configured to house the second actuation assembly.

11. The layered flow control plate of claim 10 wherein the first chamber is fluidly isolated from the second chamber.

* * * * *